United States Patent
Vautravers et al.

(10) Patent No.: US 9,969,708 B2
(45) Date of Patent: May 15, 2018

(54) METHOD FOR PRODUCING GLYCERIC ACID CARBONATE

(71) Applicant: Construction Research & Technology, GmbH, Trostberg (DE)

(72) Inventors: Nicolas Vautravers, Strasbourg (FR); Joaquim Henrique Teles, Waldsee (DE); Heimo Woelfle, Traunstein (DE); Markus Dierker, Duesseldorf (DE); Dominik Ohlmann, Mannheim (DE)

(73) Assignee: Construction Research & Technology, GmbH, Trostberg (DE)

( * ) Notice: Subject to any disclaimer, the term of this patent is extended or adjusted under 35 U.S.C. 154(b) by 0 days. days.

(21) Appl. No.: 15/520,129

(22) PCT Filed: Aug. 10, 2015

(86) PCT No.: PCT/EP2015/068361
§ 371 (c)(1),
(2) Date: Apr. 19, 2017

(87) PCT Pub. No.: WO2016/062424
PCT Pub. Date: Apr. 28, 2016

(65) Prior Publication Data
US 2017/0320847 A1    Nov. 9, 2017

(30) Foreign Application Priority Data

Oct. 23, 2014  (DE) ........................ 10 2014 221 523

(51) Int. Cl.
*C07D 317/36* (2006.01)
*C07B 41/06* (2006.01)

(52) U.S. Cl.
CPC ............ *C07D 317/36* (2013.01); *C07B 41/06* (2013.01)

(58) Field of Classification Search
CPC ............................... C07D 317/36; C07B 41/06
See application file for complete search history.

(56) References Cited

U.S. PATENT DOCUMENTS 9,309,218 B2    4/2016  Woelfle et al.
2015/0051365 A1  2/2015  Woelfle et al.

FOREIGN PATENT DOCUMENTS

WO    WO 2013/092011 A1    6/2013

OTHER PUBLICATIONS

PCT/EP2015/068361—International Search Report, dated Oct. 23, 2015. English Translation.
PCT/EP2015/068361—International Written Opinion, dated Oct. 23, 2015. English Translation.
PCT/EP2015/068361—International Preliminary Report on Patentability, dated Apr. 25, 2017. English Translation.
Gu, Ning-Yu., et al., "Preparation and Characterization of Composite Polymer Electrolytes Containing Surface-Modified Nano Silica", Chemical Journal of Chinese Universities, Jun. 2012, pp. 1295-1300, vol. 33, Issue 6. English Translation.
CASREACT Database entry XP002746142, Chemical Abstracts Service, Columbus Ohio (citing Gu, Ning-Yu., et al.).
Tojo, et al., "Heyns Oxidation," Oxidation of Primary Alcohols to Carboxylic Acids—A Guide to Current Common Practice, Basic Reactions in Organic Synthesis, 2007, pp. 43-60. Springer Science and Business Media LLC (partial).
Tojo, et al., "Heyns Oxidation," Oxidation of Primary Alcohols to Carboxylic Acids—A Guide to Current Common Practice, Basic Reactions in Organic Synthesis, 2007, pp. 43-60. Springer Science and Business Media LLC.

*Primary Examiner* — Timothy R Rozof
(74) *Attorney, Agent, or Firm* — Curatolo Sidoti Co., LPA; Joseph G. Curatolo; Salvatore A. Sidoti

(57) ABSTRACT

The present invention relates to a method for preparing a compound of the formula (I) with a specific definition of the substituent $R_3$

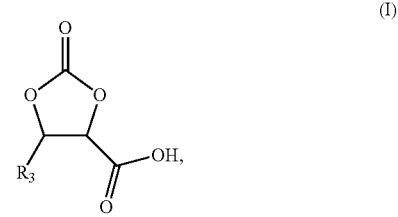

(I)

a mixture and also a corresponding application/use.

13 Claims, No Drawings

METHOD FOR PRODUCING GLYCERIC ACID CARBONATE

CROSS REFERENCE TO RELATED APPLICATIONS

This application is a national stage application of International Application No. PCT/EP2015/068361, filed 10 Aug. 2015, which claims priority from German Patent Application No. 10 2014 221 523.4, filed 23 Oct. 2014, which applications are incorporated herein by reference.

The present invention relates to a method for preparing a compound of the formula (I) with a specific definition of the substituent $R_3$

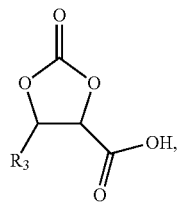

a mixture and also a corresponding application/use.

Document WO 2013/092011 A1 with the title "2-OXO-1,3-DIOXOLANE-4-CARBOXAMIDES, THEIR PREPARATION AND USE" discloses a method for preparing a compound of the formula (I), where $R_3$ is H. WO 2013/092011 A1, page 10, lines 6 to 11 discloses that glycerol carbonate (compound of the formula (II), where $R_3$ is H)

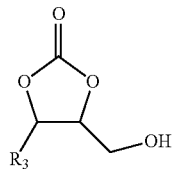

can be oxidized by (i) "N-oxide-mediated oxidation" or (ii) "aerobic oxidation". Directly after it states: "The N-oxide-mediated oxidation may be carried out with 1,3,5-trichloroisocyanuric acid and 2,2,6,6-tetramethylpiperidin-1-oxyl (TEMPO). It may also be carried out with hydrogen peroxide as an oxidant, e.g. in the presence of a manganese salt. The aerobic oxidation uses oxygen from air or oxygen in pure form as the oxidant. It is suitably carried out in the presence of at least one transition metal salt selected from Co, Mn, Cu, Fe, and mixtures thereof, preferably Mn. It is preferably carried out in a suitable solvent or in (e.g. aqueous) acetic acid" (cf. page 10, lines 13 to 20 in WO 2013/092011 A1).

The object of the present invention was to provide a method which has one, preferably more than one or particularly preferably all of the following advantages:
  relatively low operative and technical complexity,
  high degree of conversion of the reactant compounds (e.g. conversion of a compound of the formula (II)),
  high yield of product (compound of the formula (I)),
  simple operative separation of the product from the reaction medium.

This object is achieved by a method according to the invention for preparing a compound of the formula (I)

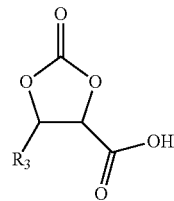

where $R_3$ is selected from H and straight-chain, branched or cyclic $C_{1-12}$-alkyl groups,
(a) with the following steps:
   providing or preparing a compound of the formula (II)

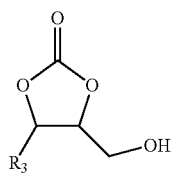

where $R_3$ has the definition selected for formula (I)
platinum-catalysed oxidation of the compound of the formula (II) with gaseous oxygen to give the compound of the formula (I).

The compound of the formula (I) is an organic acid, the carboxyl group of which dissociates in aqueous solution and results in an acidic pH.

The residue $R_3$ is selected from H and straight-chain, branched or cyclic $C_{1-12}$-alkyl groups. Preference is given to a method according to the invention (as described above, preferably as defined above as preferred), where $R_3$ is selected from the group consisting of H, straight-chain $C_{1-12}$-alkyl groups, branched $C_{1-12}$-alkyl groups and cyclic $C_{1-12}$-alkyl groups, wherein the cyclic $C_{1-12}$-alkyl groups comprise one or more alkyl substituents on the ring structure (i.e., the ring structure comprises one or more branches) or the cyclic $C_{1-12}$-alkyl groups do not comprise any alkyl substituents on the ring structure (i.e. the ring structure does not comprise any branches). $R_3$ is particularly preferably selected from H and straight-chain or branched (i.e. not cyclic) $C_{1-12}$-alkyl groups. The straight-chain, branched or cyclic alkyl groups are preferably $C_{1-10}$, preferably $C_{1-8}$, particularly preferably $C_{1-6}$-alkyl groups.

Depending on the desired product, $R_3$ is preferably selected from the group consisting of H, methyl, ethyl, propyl, isopropyl, n-butyl, isobutyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 3-methylpentyl, 3-methylpentyl, 4-methylpentyl, 2,2-dimethylbutyl, 3,3-dimethylbutyl, 2-methyl-3,3-dimethylpropyl, n-heptyl, n-octyl, n-nonyl, n-decyl, n-undecyl, n-dodecyl, cyclopentyl, cyclohexyl and cycloheptyl, particularly preferably selected from the group consisting of H, methyl, ethyl, propyl, isopropyl, n-butyl, isobutyl, n-pentyl, 2-pentyl, 3-pentyl, 2-methylbutyl, 3-methylbutyl, 3-methylbut-2-yl, 2-methylbut-2-yl, 2,2-dimethylpropyl and n-hexyl, especially selected from the group consisting of H, methyl, ethyl, propyl and isopropyl.

The gaseous oxygen to be used is preferably gaseous oxygen present in air or gaseous technical grade (pure) oxygen or atomic or molecular oxygen which is initially still chemically or physically bound and only has to be converted into released gaseous oxygen (precursors of free, gaseous oxygen). Chemically bound oxygen is oxygen bound in peroxides for example, which is released preferably by chemical reactions so that it is available as gaseous oxygen. Physically bound oxygen is, for example, adsorbed gaseous oxygen or oxygen dissolved in liquids (e.g. in water) and which can be driven out of the liquid, for example by increasing the temperature, so that it is available as gaseous oxygen. Chemically bound or physically bound oxygen therefore represents a precursor of the gaseous oxygen to be used in the method according to the invention. Particular preference is given to gaseous oxygen present in air or pure gaseous oxygen (i.e. gaseous technical grade oxygen having an oxygen content of >99%).

In one method according to the invention (as described above, preferably as defined above as preferred) additionally side reactions may occur as well as the method configuration characterized as (a). On carrying out the method according to the invention (as described above, preferably as defined above as preferred), a compound of the formula (II) for example may be converted in a side reaction into a compound of the formula (III)

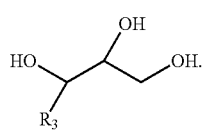

(III)

On carrying out the method according to the invention (as described above, preferably as defined above as preferred), alternatively or in addition to the abovementioned side reaction, for example a compound of the formula (I) (the desired product) or of the formula (III) may also be converted in a side reaction to a compound of the formula (IV)

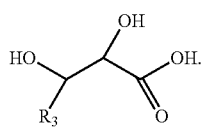

(IV)

It is not ruled out that a platinum-catalysed oxidation of the compound of the formula (III), formed in the side reaction mentioned above, with gaseous oxygen leads to a compound of the formula (IV).

A compound of the formula (IV) can be separated, for example, from the reaction mixture (or after further processing steps) and, under suitable conditions, may be converted to a compound of the formula (I) (cyclization with phosgene or dimethyl carbonate for example; analogously to a preparation of the compound of the formula (II)). In some cases therefore, preference is given to a method according to the invention (as described above, preferably as defined above as preferred) for preparing as a compound of the formula (I)

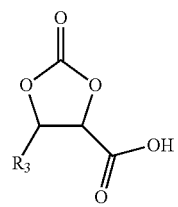

(I)

where $R_3$ is selected from H and straight-chain, branched or cyclic $C_{1-12}$-alkyl groups,
(a) with the following steps:
providing or preparing a compound of the formula (II)

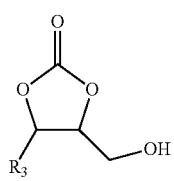

(II)

where $R_3$ has the definition selected for formula (I)
platinum-catalysed oxidation of the compound of the formula (II) with gaseous oxygen to give the compound of the formula (I)
and additionally
(b) with the following steps:
providing or preparing a compound of the formula (III)

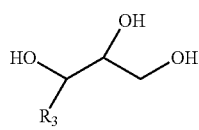

(III)

where $R_3$ has the definition selected for formula (I)
platinum-catalysed oxidation of the compound of the formula (III) with gaseous oxygen to give a compound of the formula (IV)

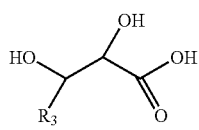

(IV)

and optionally the step of:
converting the compound of the formula (IV) to the compound of the formula (I).

The compound of the formula (IV) is converted to the compound of the formula (I) in this case, as already mentioned in the text above, preferably in the presence of dimethyl carbonate or phosgene.

Particular preference is given to a method according to the invention (as described above, preferably as defined above as preferred), wherein a catalyst is used for the platinum-catalysed oxidation comprising platinum as a solid, preferably comprising platinum as a solid on a support material, particularly preferably comprising platinum as a solid on carbon.

Particularly preferred support materials are selected from the group consisting of $Al_2O_3$, $Y_2O_3$, $Lu_2O_3$, $ZrO_2$—$Y_2O_3$, $TiO_2$, $Fe_2O_3$, $SiO_2$, zeolites, gamma-AlO(OH), carbon and mixtures thereof, carbon being a particularly preferred support material.

A particularly preferred catalyst for the platinum-catalysed oxidation is a "platinum (as solid) on carbon" catalyst (also known as supported platinum), wherein the platinum loading on carbon is preferably in the range of 4 w/w % Pt/C to 12 w/w % Pt/C, particularly preferably in the range of 5 w/w % Pt/C to 10 w/w % Pt/C. Our own investigations have shown that in some cases an undesirably high $CO_2$ formation (decarboxylation) was observed at a loading of less than 4 w/w % Pt/C.

The total amount of supported platinum in a method according to the invention (as described above, preferably as defined above as preferred) is preferably 2.5 to 10 mol %, preferably 4 to 8 mol %, particularly preferably 4 to 6 mol %, based in each case on the total amount of the compound of the formula (II).

Particular preference is given to a method according to the invention (as described above, preferably as defined above as preferred), wherein for the platinum-catalysed oxidation a "platinum (as solid) on carbon" catalyst is used for the oxidation with gaseous oxygen, in which
- the platinum loading on carbon is in the range of 4 w/w % Pt/C to 12 w/w % Pt/C, preferably in the range of 5 w/w % Pt/C to 10 w/w % Pt/C and
- the total amount of supported platinum (as described above, preferably as defined above as preferred) is 2.5 to 10 mol %, preferably 4 to 8 mol %, particularly preferably 4 to 6 mol %, based in each case on the total amount of the compound of the formula (II).

Our own investigations have revealed that good results (acceptable yields and acceptable conversions) are then regularly achieved when there is a defined ratio of platinum to the total amount of the compound of the formula (II). Preference is therefore given to a method according to the invention (as described above, preferably as defined above as preferred), wherein at the start of the platinum-catalysed oxidation step the molar ratio of the platinum used to the compound of the formula (II) is greater than 2:100, preferably greater than 3:100.

Particular preference is given to a method according to the invention (as described above, preferably as defined above as preferred), where $R_3$ is hydrogen. In this case, the compound of the formula (I) is glyceric acid carbonate, the compound of the formula (II) is glycerol carbonate (the compound of the formula (III) is glycerol and the compound of the formula (IV) is glyceric acid). What is stated in the text above and below in relation to preferred configurations of the method according to the invention applies particularly to a preferred method according to the invention in which $R_3$ is H.

Particular preference is given to a method according to the invention (as described above, preferably as defined above as preferred), wherein the platinum-catalysed oxidation step is carried out in an aqueous medium. An aqueous medium has proven to be advantageous in practice since the compounds of the formulae (I) and (II) routinely have sufficient stability (stability to hydrolysis for example) in an aqueous medium for the present purposes or the compound of the formula (II) has sufficiently good reactivity. In addition, an aqueous medium is simple to provide and, at the end of the method according to the invention, comparatively simple to work-up in order to isolate the compound of the formula (I).

Preference is given to a method according to the invention (as described above, preferably as defined above as preferred), wherein the platinum-catalysed oxidation step is carried out at least intermittently, preferably for most of the time, at a temperature in the range of 50 to 90° C., preferably in the range of 50 to 82° C., particularly preferably in a range of 68 to 82° C. The platinum-catalysed oxidation step is particularly preferably carried out at a temperature in the range of 50 to 90° C., preferably in the range of 50 to 82° C., particularly preferably in a range of 68 to 82° C.

Temperatures in the range of 50 to 90° C., preferably in the range of 50 to 82° C., particularly preferably in the range of 68 to 82° C., are particularly advantageous since such temperatures may be achieved at standard atmospheric pressure. This enables a comparatively simple method configuration. Temperatures <50° C. lead to a very slow reaction course which is particularly uneconomic. Temperatures greater than 82° C. lead to increasing decomposition ($CO_2$ formation, hydrolysis) of the reactants or products and therefore result in a deteriorating yield. This effect is particularly pronounced if the temperatures exceed 90° C.

As already mentioned above, the compounds of the formulae (I) and (II) have sufficient stability to hydrolysis in an aqueous medium for the present purposes. This stability to hydrolysis is not only dependent on the solvent(s) used (preferably water) but also on the pH of the relevant aqueous medium (particularly when using water as the sole solvent). As also already detailed above, the compound of the formula (I) produced is an organic acid, the carboxyl group of which dissociates in the presence of water already leading to a lowering of the pH in the aqueous medium during the course of the reaction. pH values greater than 6, particularly >7, have an adverse effect on the stability of glycerol carbonate (compound of the formula (II), where $R_3$ is H) and glyceric acid carbonate (compound of the formula (I), where $R_3$ is H). The susceptibility to hydrolysis increases with increasing pH. Conversely, a comparatively low pH (less than 6) stabilizes the compounds of the formulae (I) and (II), where $R_3$ is in each case preferably H.

Particular preference is therefore given to a method according to the invention (as described above, preferably as defined above as preferred), wherein at the start of the platinum-catalysed oxidation step in the aqueous medium the pH is 7 or <7, preferably the pH is in a range from 4 to 7, preferably the pH is in a range from 4 to 6.

In a preferred method according to the invention, the platinum-catalysed oxidation step is carried out at least intermittently, preferably for most of the time, at a temperature in the range of 50 to 90° C., preferably in the range of 50 to 82° C., particularly preferably in a range of 68 to 82° C. In these preferred method configurations, the pH in the aqueous medium at the start of the oxidation is preferably in the range of 4 to 7, preferably in the range of 4 to 6. At a temperature in the range of 50 to 90° C., preferably in the range of 50 to 82° C., particularly preferably in the range of 68 to 82° C., and a pH in the range of 4 to 7, preferably in the range of 4 to 6 (based in each case on the start of the oxidation), the compound of the formula (II) still shows sufficiently high oxidizability and stability with respect to undesired side reactions and can therefore be readily converted to a compound of the formula (I).

Our own investigations have highlighted that it is routinely advantageous that the method according to the invention is carried out such that the pH in the aqueous medium is the result of the dissociation of the compound of the formula (I) (and, if applicable, also of the formula (IV)). As already detailed above, the presence of the compound of the formula (I) in the aqueous medium leads particularly to a lowering of the pH until (at least substantially) a pH is reached which corresponds to the intrinsic pH of this compound (in particular the compound of the formula (I), where $R_3$ is preferably H) in the aqueous medium. The intrinsic pH of a compound is the pH which exists in an aqueous medium at a given concentration of this compound and due to the pKa associated with this compound. Preference is given to a method according to the invention (as defined above, preferably as defined above as preferred), wherein the platinum-catalysed oxidation step is carried out such that, on formation of the compound of the formula (I), the pH in the aqueous medium decreases, preferably by at least 2 pH units, particularly preferably by at least 3 pH units, more preferably by at least 4 pH units, especially preferably by 6 pH units.

A pH drop of 2.5 pH units occurs for example when, starting from an initial pH of 4.5 for example, the pH of the aqueous medium decreases to 2 during the oxidation (cf. the examples further below in the text). Particular preference is given to carrying out the platinum-catalysed oxidation step such that, on formation of the compound of the formula (I) (where $R_3$ is preferably H), the pH in the aqueous medium is in the range of 2 to 0, preferably in the range of 1.4 to 0.2.

It has been shown in our own investigations, surprisingly, that the supported platinum catalyst preferably used (for preferred catalysts see further below in the text) in the method according to the invention (as defined above, preferably as defined above as preferred) in an aqueous medium with the pH values described above still has sufficient activity. Under these conditions, compounds of the formulae (I) and (II), where $R_3$ is preferably H, are for the present purposes substantially protected from hydrolysis. As already mentioned above, it was an object of the present invention to provide a method which can be carried out simply and without relatively great operative complexity. Since it has been shown, surprisingly, that the preferred supported platinum catalyst to be used at the pH values mentioned above still has sufficient activity, an ongoing determination and, if appropriate, adjustment of the pH of the aqueous medium in the method according to the invention (as defined above, preferably as defined above as preferred) is not required. Typically, the pH at less acidic conditions is maintained by addition of bases in a certain pH range (e.g. in Heyns oxidations). However, in the method according to the invention, no further measures have to be undertaken in order to counteract the self-adjusting intrinsic pH in the aqueous medium by continuous or stepwise addition of a base. It is also unnecessary to use an aqueous medium with a buffer system in order to counteract the pH decrease occurring during the reaction by dissociation of the acid formed as product. This simplifies the method procedure and reduces the costs required to carry out the method. Particular preference is therefore given to a method according to the invention (as described above, preferably as defined above as preferred), wherein the platinum-catalysed oxidation step is carried out without addition of base or buffer.

It has been shown in our own investigations that a particularly good yield of the compound of the formula (I) is routinely achieved even though the pH in the aqueous medium is low (see the preceding embodiments). In some cases, preference is given to a method according to the invention (as described above, preferably as defined above as preferred), wherein the platinum-catalysed oxidation step is not terminated before the pH (starting from higher pH values) falls below 2, preferably below 1, particularly preferably below 0.5, wherein at the start of the platinum-catalysed oxidation step in the aqueous medium the pH is 7 or less than 7, preferably the pH is in a range of 4 to 7, preferably the pH is in a range of 4 to 6 or wherein the platinum-catalysed oxidation step is carried out at least until (starting from higher pH values) the pH falls below 2, preferably below 1, particularly preferably below 0.5, wherein at the start of the platinum-catalysed oxidation step in the aqueous medium the pH is 7 or less than 7, preferably the pH is in a range of 4 to 7, preferably the pH is in a range of 4 to 6.

It is therefore particularly advantageous to carry out the method according to the invention (as described above, preferably as defined above as preferred) preferably such that at least a target pH is reached before the reaction is terminated (starting from a particular higher initial pH). A procedure of this kind is particularly advantageous when the method according to the invention is carried out as a batch process. The platinum-catalysed oxidation step is preferably not terminated before the pH (starting from higher pH values) falls below 2, preferably below 1, particularly preferably below 0.5 (wherein at the start of the platinum-catalysed oxidation step in the aqueous medium the pH is 7 or less than 7, preferably the pH is in a range of 4 to 7, preferably the pH is in a range of 4 to 6), or wherein the platinum-catalysed oxidation step is carried out at least until (starting from higher pH values) the pH falls below 2, preferably below 1, particularly preferably below 0.5 (wherein at the start of the platinum-catalysed oxidation step in the aqueous medium the pH is 7 or <7, preferably the pH is in a range of 4 to 7, preferably the pH is in a range of 4 to 6), wherein the platinum-catalysed oxidation step (in each case based on the two alternatives mentioned above) is carried out at least intermittently, preferably for most of the time, at a temperature in the range of 50 to 90° C., preferably in the range of 50 to 82° C., particularly preferably in a range of 68 to 82° C.

Particular preference is given to a method according to the invention (as described above, preferably as defined above as preferred), wherein the yield of the compound of the formula (I) is 90% or higher after the platinum-catalysed oxidation step has been terminated and the pH of the aqueous medium has preferably fallen below 0.5 (cf. the examples in the text below).

Particular preference is given to a method according to the invention (as described above, preferably as defined above as preferred), wherein the platinum-catalysed oxidation step is not terminated before the pH of the aqueous medium has reached the intrinsic pH (or the platinum-catalysed oxidation step is carried out until the pH of the aqueous medium substantially corresponds to the intrinsic pH of the compound of the formula (I)), wherein the platinum-catalysed oxidation step is preferably carried out at least intermittently, preferably for most of the time, at a temperature in the range of 50 to 90° C., preferably in the range of 50 to 82° C., particularly preferably in a range of 68 to 82° C.

As already detailed in the text above, the platinum-catalysed oxidation is carried out with gaseous oxygen. The oxygen for the oxidation of the compound of the formula (II) (optionally also for the oxidation of a compound of the formula (III)) can be supplied here in various ways. Particular preference is given to a method according to the invention (as described above, preferably as defined above as preferred), wherein the platinum-catalysed oxidation step is carried out in such a way that the gaseous oxygen is introduced into the aqueous medium. Particular preference is given to a method according to the invention (as described above, preferably as defined above as preferred), wherein the gaseous oxygen is introduced into the aqueous medium in the form of gaseous air or pure gaseous oxygen (e.g. technical grade oxygen having an oxygen content greater than 99%). The gas introduced (e.g. gaseous air or pure gaseous oxygen) is preferably introduced into the aqueous medium such that the gas introduced flows through the aqueous medium and thereby preferably the contact time with the aqueous medium is maximal.

Preference is given to a method according to the invention (as described above, preferably as defined above as preferred), wherein the platinum-catalysed oxidation step is carried out at atmospheric pressure. Depending on other applications it may be preferable to carry out the method according to the invention (as described above, preferably as defined above as preferred) such that the platinum-catalysed oxidation step is carried out at a pressure in a range of 1 to 50 bar, preferably in a range of 1 to 10 bar, particularly preferably in a range of 1 to 2 bar.

Particular preference is given to a method according to the invention (as described above, preferably as defined above as preferred), wherein the compounds with the formulae (I) to (IV) (particularly the compounds of the formulae (I) and (II)) are dissolved in an aqueous medium (aqueous solution) (preferably an aqueous medium as described above, preferably as defined above as preferred). This is particularly advantageous if a preferred supported platinum catalyst (for preferred catalysts see further below in the text) is used for the platinum-catalysed oxidation. In this case, the heterogeneous platinum catalyst can be removed from the aqueous solution by simple mechanical separation methods (e.g. by filtration, centrifugation and/or sedimentation). If a complete or almost complete conversion of a compound of the formula (II) to a compound of the formula (I) takes place, the reaction medium separated from the catalyst (e.g. the filtrate) comprises exclusively or almost exclusively the desired reaction product of the formula (I). Under these conditions, the product of the formula (I) can be obtained in a simple manner and without major operative, technical complexity. In a subsequent step, the solvent water is preferably removed (evaporated), preferably under reduced pressure (e.g. on a rotary evaporator).

The present invention also relates to the application (or the use) of the Heyns oxidation for preparing the compound of the formula (I). In accordance with the invention, the present invention therefore relates to the application (or the use) of the Heyns oxidation
(a) for oxidizing a compound of the formula (II)

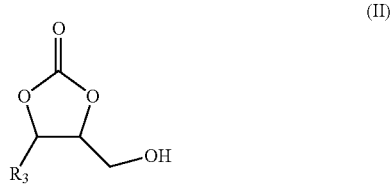

where $R_3$ is selected from H and straight-chain, branched or cyclic $C_{1-12}$-alkyl groups,
wherein the Heyns oxidation is carried out without addition of base or buffer.

What is stated above in relation to the method according to the invention applies accordingly to the application (or use) according to the invention.

As already mentioned in the text above (and without being bound to this assumption), it is not ruled out in the method according to the invention that a compound of the formula (III) (which may be present in the preferred aqueous medium of the method according to the invention) is converted to a compound of the formula (IV) by means of the platinum-catalysed oxidation step. In this case, application (or use) according to the invention of the Heyns oxidation is preferred
(a) for oxidizing a compound of the formula (II)

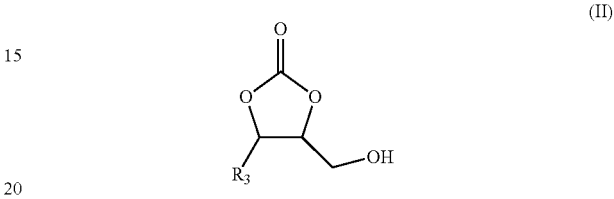

where $R_3$ is selected from H and straight-chain, branched or cyclic $C_{1-12}$-alkyl groups,
and additionally
(b) for oxidizing a compound of the formula (III)

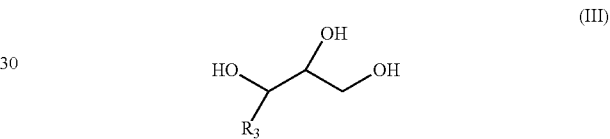

where $R_3$ has the definition selected for formula (II),
wherein the Heyns oxidation is carried out in each case without addition of base or buffer.

The "Heyns oxidation" refers to the oxidation of organic primary alcohols to organic acids in the presence of oxygen and platinum in aqueous media, particularly at a basic pH. Details for the Heyns reaction can be found in the text book "Oxidation of Primary Alcohols to Carboxylic Acids, A Guide to Current Common Practice" by Gabriel Tojo and Marcos Fernandez on pages 43 to 60.

The application (or use) of the Heyns oxidation therefore results in a method (preferably in a preferred method according to the invention if preferred temperatures and/or pH values are used), in which the primary hydroxyl group of a compound of the formula (II) (and if applicable a compound of the formula (III)) is converted into a carboxyl group by means of oxidation in the presence of gaseous oxygen (resulting in a compound of the formula (I) (and if applicable a compound of the formula (IV)). The oxidation reaction proceeding in this case comprises the oxidation of the hydroxyl group to an aldehyde group and the subsequent oxidation of the aldehyde group to a carboxyl group. If the oxidation step is carried out under anhydrous conditions, complete oxidation to the carboxyl group does not take place, rather the primary hydroxyl group is oxidized only as far as the aldehyde group.

Particular preference is given to the application (or use) of the Heyns oxidation (as described above, preferably as defined above as preferred), wherein the oxidation step is carried out at least intermittently, preferably for most of the time, at a temperature in the range of 50 to 90° C., preferably in the range of 50 to 82° C., particularly preferably in the range of 68 to 82° C.

Particular preference is given to the application (or use) according to the invention of the Heyns oxidation (as described above, preferably as defined above as preferred), wherein (independently of the temperature mentioned above or in addition to the temperature mentioned above) the oxidation step is not terminated before the pH (starting from higher pH values) falls below 2, preferably below 1, particularly preferably below 0.5, wherein at the start of the platinum-catalysed oxidation step in the aqueous medium the pH is 7 or less than 7, preferably the pH is in a range of 4 to 7, preferably the pH is in a range of 4 to 6 or wherein the platinum-catalysed oxidation step is carried out at least until (starting from higher pH values) the pH falls below 2, preferably below 1, particularly preferably below 0.5, wherein at the start of the platinum-catalysed oxidation step in the aqueous medium the pH is 7 or <7, preferably the pH is in a range of 4 to 7, preferably the pH is in a range of 4 to 6.

The present invention also relates to a mixture comprising
a catalyst comprising platinum as a solid, preferably comprising platinum as a solid on a support material, particularly preferably comprising platinum as a solid on carbon,
and also
one or more compounds selected from the group consisting of
(a) compounds of the formula (II)

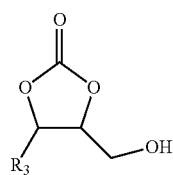

(II)

where $R_3$ is selected from H and straight-chain, branched or cyclic $C_{1-12}$-alkyl groups
and optionally one or more compounds selected from the group consisting of
(b) compounds of the formula (III)

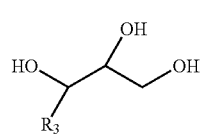

(III)

where $R_3$ is selected from H and straight-chain, branched or cyclic $C_{1-12}$-alkyl groups.

The mixture according to the invention (as described above) preferably comprises both one or more (preferably one, particularly preferably a compound of the formula (II), where $R_3$ is H) compounds of the formula (II) and one or more (preferably one, particularly preferably a compound of the formula (III), where $R_3$ is H) compounds of the formula (III), wherein the quantitative proportion of the compound of the formula (II) is preferably 95% or greater than 95%, preferably 97% or greater than 97%, based on the total amount of compounds of the formulae (II) and (III).

What is stated above in relation to the method according to the invention or what is stated above in relation to the application of the Heyns oxidation according to the invention applies accordingly to the mixture according to the invention.

The mixture according to the invention described above is preferably used at the starting time in a method according to the invention (as described above, preferably as defined above as preferred) or preferably at the starting time in the application (or use) of the Heyns oxidation according to the invention (as described above, preferably as defined above as preferred) (e.g. in a method configuration known as a batch process).

As already explained in the text above, side reactions routinely occur in a method according to the invention (for specific side reactions see further above in the text).

In some cases, preference is given to a mixture according to the invention (as described above, preferably as defined above as preferred) comprising
a catalyst comprising platinum as a solid, preferably comprising platinum as a solid on a support material, particularly preferably comprising platinum as a solid on carbon,
one or more (preferably one) compound of the formula (II)

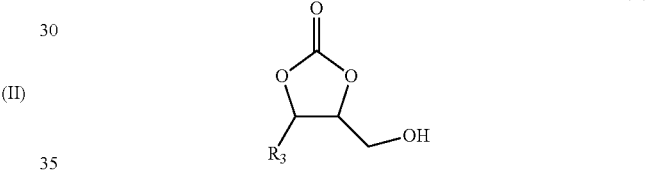

where $R_3$ is selected from H and straight-chain, branched or cyclic $C_{1-12}$-alkyl groups
and also
(a) one or more (preferably one) compounds of the formula (I)

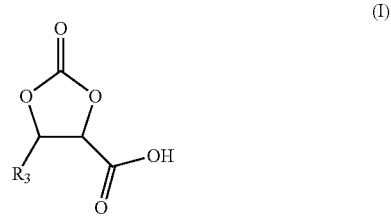

(I)

where $R_3$ is selected from H and straight-chain, branched or cyclic $C_{1-12}$-alkyl groups
and also preferably
(b) one or more (preferably one) compounds of the formula (III)

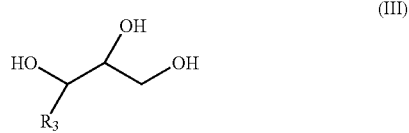

(III)

where $R_3$ is selected from H and straight-chain, branched or cyclic $C_{1-12}$-alkyl groups
and preferably
(c) one or more (preferably one) compounds of the formula (IV)

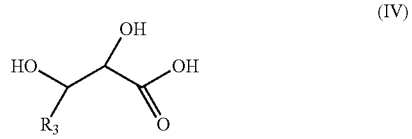

where $R_3$ is selected from H and straight-chain, branched or cyclic $C_{1-12}$-alkyl groups.

The preferred mixture according to the invention described above is preferably obtained as a reaction mixture or used in a method according to the invention (as described above, preferably as defined above as preferred) or preferably in the application (or use) of the Heyns oxidation according to the invention (as described above, preferably as defined above as preferred) (e.g. in a continuous method configuration).

The present invention also relates to the use of a mixture according to the invention (as described above, preferably as defined above as preferred) comprising
a catalyst comprising platinum as a solid, preferably comprising platinum as a solid on a support material, particularly preferably comprising platinum as a solid on carbon,
and also
one or more compounds selected from the group consisting of
(a) compounds of the formula (II)

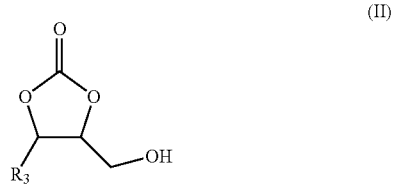

where $R_3$ is selected from H and straight-chain, branched or cyclic $C_{1-12}$-alkyl groups
and optionally one or more compounds selected from the group consisting of
(b) compounds of the formula (III)

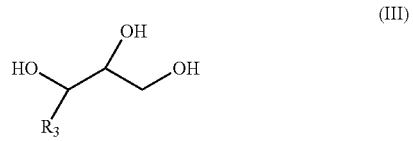

where $R_3$ is selected from H and straight-chain, branched or cyclic $C_{1-12}$-alkyl groups
in a method for preparing a compound of the formula (I), preferably in a method according to the invention (as described above, preferably as defined above as preferred) for preparing a compound of the formula (I). Particular preference is given to the use according to the invention of the mixture according to the invention described above, wherein the mixture according to the invention comprises both one or more (preferably one, particularly preferably a compound of the formula (II), where $R_3$ is H) compounds of the formula (II) and one or more (preferably one, particularly preferably a compound of the formula (III), where $R_3$ is H) compounds of the formula (III).

The invention is illustrated below by means of examples.

EXAMPLES

1. General Experimental Setup:

In a first step, a "platinum on carbon" catalyst was added to an aqueous glycerol carbonate solution (compound of the formula (II), where $R_3$ is H, in water) (the details for the catalyst below are molar based on glycerol carbonate).

In a second step, the solution with added heterogeneous catalyst (hereinafter referred to as suspension) was heated to the desired temperature and oxygen (99.995%, Air Liquide) was introduced into the suspension via a frit at the desired pressure or the desired flow rate (cf. Table 1) for the period of the experimental procedure.

In a third step, (a) the ratio of compound of the formula (I) to compound of the formula (II) and (b) the ratio of compound of the formula (I) to compound of the formula (IV) was determined by $^1H$— and $^{13}C$-NMR at various time points. For further details and descriptions of the experimental parameters see section 2 and Table 1 below.

2. Specific Experimental Parameters and Results:

Details and experimental parameters are summarized in Table 1 below, with the following meanings:
"#" example number
"$O_2$ [l/h]" oxygen flow rate (in the open reaction procedure; relates to examples 1 to 12)
"Pressure [bar]" oxygen pressure in the reactor (in the closed reaction procedure; relates to examples 13 to 15)
"GC [w/w %]" glycerol carbonate concentration in water
"Pt [mol %]" amount of supported platinum used based on the total amount of glycerol carbonate in the suspension
"Pt/C [w/w %]" platinum loading of the heterogeneous catalyst
"Output [%]" crude yield based on 100% conversion, wherein crude yield refers to the suspension residue after removal of the catalyst by filtration and evaporation of the readily volatile components
"(I):(II)" quantitative ratio of glyceric acid carbonate to glycerol carbonate (degree of conversion and selectivity)
"(I):(IV)" quantitative ratio of glyceric acid carbonate to glyceric acid (degree of selectivity and extent of decomposition reaction).

Platinum on carbon catalysts from Sigma Aldrich with the following product numbers were used as catalysts:
Pt/C [w/w %] 10: product number: 80980–PVC [w/w %] 5: product number: 80982

TABLE 1

| # | $O_2$ [l/h] | Pressure [bar] | T [° C.] | t [h] | GC [w/w %] | Pt [mol %] | Pt/C [w/w %] | Output [%] | (I):(II) | (I):(IV) |
|---|---|---|---|---|---|---|---|---|---|---|
| 1 | 22.5 | — | 70 | 12 | 8.3 | 5 | 10 | 0 | — | — |
| 2 | 22.5 | — | 70 | 2 | 8.3 | 5 | 10 | — | 81 | 95 |
| 3 | 22.5 | — | 70 | 3 | 8.3 | 5 | 10 | — | 88 | 92 |
| 4 | 22.5 | — | 70 | 4 | 8.3 | 5 | 10 | 93 | 92 | 92 |
| 5 | 22.5 | — | 80 | 4 | 8.3 | 5 | 10 | 70 | 99 | 92 |

TABLE 1-continued

| # | O$_2$ [l/h] | Pressure [bar] | T [° C.] | t [h] | GC [w/w %] | Pt [mol %] | Pt/C [w/w %] | Output [%] | (I):(II) | (I):(IV) |
|---|---|---|---|---|---|---|---|---|---|---|
| 6 | 22.5 | — | 90 | 4 | 8.3 | 5 | 10 | 60 | 99 | 92 |
| 7 | 22.5 | — | 90 | 2 | 8.3 | 5 | 10 | — | 96 | 96 |
| 8 | 22.5 | — | 90 | 2 | 12 | 5 | 10 | — | 60 | 90 |
| 9 | 22.5 | — | 90 | 2 | 15.3 | 5 | 10 | — | 16 | 89 |
| 10 | 65.0 | — | 70 | 2 | 8.3 | 5 | 10 | — | 74 | 94 |
| 11 | 65.0 | — | 70 | 4 | 8.3 | 5 | 10 | — | 87 | 93 |
| 12 | 22.5 | — | 70 | 2 | 8.3 | 5 | 10 | — | 81 | 95 |
| 13 | — | 2 | 70 | 2 | 8.3 | 5 | 5 | 55 | 91 | 89 |
| 14 | — | 2 | 70 | 2 | 8.3 | 5 | 10 | 80 | 90 | 92 |
| 15 | — | 2 | 70 | 2 | 8.3 | 2.5 | 10 | 78 | 69 | 91 |

In examples 2, 3 and 7 to 12, the "output" was not determined.

Example 1 shows that after a reaction time of 12 hours all reactants were completely decomposed to $CO_2$. Particular preference is given to a reaction time of 2 to 4 hours.

Example 5 shows (compared to examples 4 and 6) that a selectivity optimum with moderate output losses was achieved at a particularly preferred reaction temperature of 80° C. and a preferred reaction time of 4 hours.

Example 7 shows (compared to examples 8 and 9) that a glycerol carbonate concentration of 8.3 w/w % results in very high "(I):(II)" and "(I):(IV)" ratios compared to concentrations of 12 and 15.3 w/w % in examples 8 and 9 respectively, at otherwise identical reaction time.

Examples 2, 10 and 11 show that an increase of the oxygen flow rate results in no notable increase in the "(I):(II)" and "(I):(IV)" ratios (neither at a reaction time of 2 nor of 4 hours).

In contrast, examples 12 and 14 show that an increase in pressure in the reactor (i.e. in the closed reaction procedure) leads to an increase in the "(I):(II)" ratio.

The results of the examples conducted shown above show that the platinum loading of the heterogeneous catalyst influences the reaction parameters reaction time and reaction temperature ("t" and "T") but not the quality of the reaction (read off by the "(I):(II)" and "(I):(IV)" ratios). For instance, examples 13 and 14 show that the reaction using a catalyst with reduced loading (example 13) results in very similar "(I):(II)" and "(I):(IV)" ratios but leads to a distinctly lower output (at identical reaction time).

Examples 14 and 15 show that a reduction in the absolute amount of platinum (cf. column Pt[mol %]) negatively affects the "(I):(II)" ratio.

According to Table 1, examples 4, 5 and 14 represent particularly preferred method procedures.

In all oxidation reactions carried out it was observed that the pH of the respective aqueous medium after 120 minutes was <0.5, starting from an initial pH in the range of 4 to 5 (at "t"=0 hours and the respective temperatures stated in each case in Table 1). The pH therefore fell in each of the examples by at least 3 pH units. A base or a buffer was not added to any of the respective suspensions.

The course of the pH is shown in more detail in Table 2 below for three selected example reactions. The example reaction shown in Table 2 conducted at a temperature of 70° C. corresponds to examples 10 and 11 in Table 1. The example reaction shown in Table 2 conducted at a temperature of 80° C. corresponds to example 5 and the example reaction conducted at 90° C. corresponds to example 6 in Table 1.

TABLE 2

| 70° C. | | | | 80° C. | | | | 90° C. | | | |
|---|---|---|---|---|---|---|---|---|---|---|---|
| Time [min] | (I):(II) | (I):(IV) | pH | Time [min] | (I):(II) | (I):(IV) | pH | Time [min] | (I):(II) | (I):(IV) | pH |
| 0 | 0 | 0 | 5.9 | 0 | 0 | 0 | 4.3 | 0 | 0 | 0 | 4.8 |
| 60 | 59 | 100 | 0.5 | 30 | 33 | 100 | 0.8 | 30 | 21 | 100 | 0.9 |
| 120 | 74 | 94 | 0.6 | 60 | 68 | 94 | 0.6 | 60 | 55 | 89 | 0.4 |
| 180 | 82 | 93 | 0.4 | 90 | 84 | 93 | 0.2 | 90 | 61 | 88 | 0.4 |
| 240 | 87 | 93 | 0.4 | 120 | 91 | 95 | 0.2 | 120 | 85 | 90 | 0.4 |
| 300 | 92 | 92 | 0.4 | 150 | 94 | 93 | 0.2 | 150 | 95 | 94 | 0.4 |
| 360 | 94 | 89 | 0.3 | 180 | 98 | 93 | 0.2 | 180 | 99 | 94 | 0.4 |
| 420 | 96 | 89 | 0.2 | 210 | 99 | 93 | 0.1 | 210 | 99 | 92 | 0.4 |
| 480 | 100 | 87 | 0.2 | 240 | 99 | 92 | 0.1 | 240 | 99 | 92 | 0.4 |

In addition, the influence of stabilizing the pH was investigated. In example 16 the pH was buffered to pH=5.5 during the reaction while in example 17 the pH was not stabilized. Further details and experimental parameters are summarized in Table 3 below.

TABLE 3

| # | O$_2$ [l/h] | Pressure [bar] | T [° C.] | t [h] | GC [w/w %] | Pt [mol %] | Pt/C [w/w %] | Buffering [pH] | (I):(II) | (I):(IV) |
|---|---|---|---|---|---|---|---|---|---|---|
| 16 | 22.5 | — | 90 | 5 | 2.5 | 2.5 | 10 | 5.5 | 41 | 34 |
| 17 | 22.5 | — | 90 | 5 | 2.5 | 2.5 | 10 | — | 98 | 94 |

Comparison of examples 16 and 17 shows that much higher conversions and selectivities can be achieved without buffering.

The invention claimed is:

1. A method for preparing a compound of the formula (I)

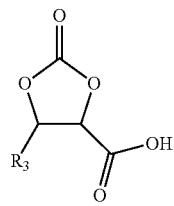

(I)

where $R_3$ is selected from H and straight-chain, branched or cyclic $C_{1-12}$-alkyl groups, the method comprising:
providing or preparing a compound of the formula (II)

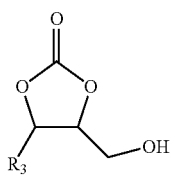

(II)

where $R_3$ has the definition selected for formula (I), and carrying out platinum-catalysed oxidation of the compound of the formula (II) with gaseous oxygen to give the compound of the formula (I).

2. The method according to claim 1, wherein a catalyst is used for the platinum-catalysed oxidation comprising platinum as a solid, optionally comprising platinum as a solid on a support material, further optionally comprising platinum as a solid on carbon.

3. The method according to claim 1, where $R_3$ is hydrogen.

4. The method according to claim 1, wherein the platinum-catalysed oxidation is carried out in an aqueous medium.

5. The method according to claim 4, wherein at the start of the platinum-catalysed oxidation in the aqueous medium the pH is 7 or <7.

6. The method according to claim 4, wherein the platinum-catalysed oxidation is carried out such that, on formation of the compound of the formula (I), the pH in the aqueous medium decreases, optionally by at least 2 pH units.

7. The method according to claim 4, wherein the platinum-catalysed oxidation is carried out without addition of base or buffer.

8. The method according to claim 4, wherein the platinum-catalysed oxidation is carried out at least until the pH falls below 2, wherein at the start of the platinum-catalyzed oxidation in the aqueous medium the pH is 7 or less than 7.

9. The method according to claim 1, wherein at the start of the platinum-catalysed oxidation the molar ratio of the platinum used to the compound of the formula (II) is greater than 2:100.

10. The method according to claim 1, wherein the platinum-catalysed oxidation is carried out at least intermittently, optionally for most of the time, at a temperature in the range of 50 to 90° C.

11. The method according to claim 4, wherein the platinum-catalysed oxidation is carried out in such a way that the gaseous oxygen is introduced into the aqueous medium.

12. A process comprising carrying out Heyns oxidation
(a) for oxidizing a compound of the formula (II)

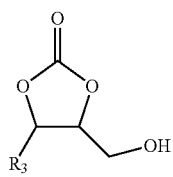

(II)

where $R_3$ is selected from H and straight-chain, branched or cyclic $C_{1-12}$-alkyl groups,
wherein the Heyns oxidation is carried out without addition of base or buffer.

13. A mixture comprising
a catalyst comprising platinum as a solid, optionally comprising platinum as a solid on a support material, further optionally comprising platinum as a solid on carbon,
and also
one or more compounds selected from the group consisting of
(a) compounds of the formula (II)

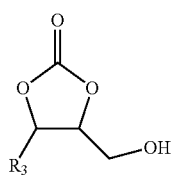

(II)

where $R_3$ is selected from H and straight-chain, branched or cyclic $C_{1-12}$-alkyl groups,
and optionally one or more compounds selected from the group consisting of
(b) compounds of the formula (III)

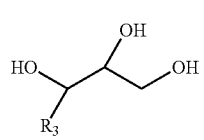

(III)

where $R_3$ is selected from H and straight-chain, branched or cyclic $C_{1-12}$-alkyl groups.

* * * * *